United States Patent [19]

Zengel et al.

[11] 4,342,707

[45] Aug. 3, 1982

[54] PROCESS FOR THE PREPARATION OF BIS-N-CHLORAMIDES

[75] Inventors: Hans-Georg Zengel, Kleinwallstadt; Manfred Bergfeld, Erlenbach, both of Fed. Rep. of Germany

[73] Assignee: Akzona Incorporated, Asheville, N.C.

[21] Appl. No.: 947,795

[22] Filed: Oct. 2, 1978

Related U.S. Application Data

[63] Continuation of Ser. No. 651,085, Jan. 21, 1976, abandoned.

[30] Foreign Application Priority Data

Jan. 22, 1975 [DE] Fed. Rep. of Germany ....... 2502411

[51] Int. Cl.$^3$ .............................................. C07C 51/58
[52] U.S. Cl. .................................. 260/543 A; 564/160
[58] Field of Search ....................... 260/543 A, 561 R; 564/160

[56] References Cited

U.S. PATENT DOCUMENTS

| | | | |
|---|---|---|---|
| 3,657,324 | 4/1972 | Sheppard et al. | 260/543 A |
| 3,746,760 | 7/1973 | Sheppard et al. | 260/543 A |
| 3,897,498 | 7/1975 | Zengel et al. | 260/578 |
| 3,914,267 | 10/1975 | Rennie et al. | 260/543 A |
| 3,917,688 | 11/1975 | Barton et al. | 260/543 A |
| 3,965,172 | 6/1976 | Zengel et al. | 260/543 A |

FOREIGN PATENT DOCUMENTS 909455 9/1957 Fed. Rep. of Germany ... 260/543 A

OTHER PUBLICATIONS

Rayon and Synthetic and Rayon Staple, 29, p. 43 (1951).

*Primary Examiner*—Natalie Trousof
*Assistant Examiner*—Frederick W. Pepper
*Attorney, Agent, or Firm*—Francis W. Young; Robert F. Green

[57] ABSTRACT

Bis-N-chloramides of saturated aliphatic dicarboxylic acids are prepared by chlorinating a saturated aliphatic dicarboxylic diamide, the aliphatic residue of which has 4 to 40 carbon atoms, in an aqueous inorganic acid medium, at a temperature between 0° and 40° C.; the chlorination is advantageously carried out in presence of an inorganic salt.

6 Claims, No Drawings

PROCESS FOR THE PREPARATION OF BIS-N-CHLORAMIDES

This is a continuation of application Ser. No. 651,085 filed Jan. 21, 1976 now abandoned.

BACKGROUND OF THE INVENTION

The present invention relates to the preparation of saturated aliphatic dicarboxylic acid bis-N-chloramides.

N-chloramides of monocarboxylic acids are easily, and with a high yield, accessible through the chlorination of appropriate monocarboxylic acid amines. However, if these processes known for monoamides are applied to aliphatic dicarboxylic acid diamides, one generally obtains the desired bis-N-chloramides only with a low yield. Only pursuant to a process described in German Pat. No. 909 455, which was especially developed for the preparation of bis-N-chloramides, it is possible to obtain higher yields in the case of pimelic acid diamide and adipic acid diamide, if chlorination is carried out either in aqueous-alkaline media, in glacial acetic acid or other organic acids with addition of alkali salts or salts of the alkaline earth metals of these acids or also in other solvents, whereby, however, a hydrogen halide must always be added as acceptor.

Conversion in an alkaline medium is disadvantageous for several reasons. The obtainable products are non-uniform, they contain unreacted diamide, furthermore dicarboxylic acid formed through hydrolysis of the diamide and the bis-N-chloramide, as well as bis-N-dichloramides formed through perchlorination of the bis-N-chloramide. Bis-N-dichloramides are also formed during chlorination in organic acids or other organic solvents in the presence of hydrogen halide acceptors. They decompose during boiling, thereby forming extremely explosive decomposition products (Rayon plus Synthetic plus Rayon Staple, 29, page 43 (1951) and thus considerably endanger the execution of this known process.

According to another version described in German Pat. No. 909 455, bis-N-chloramides are allegedly obtainable with almost quantitative yield if the dicarboxylic acid diamide is admixed in the dry state with an agent that will bond hydrogen halide, preferably sodium bicarbonate, and chlorine vapors are conducted over the dry mixture. However, these methods as well are not suitable for the industrial-scale preparation of bis-N-chloramides: the reaction mix cakes during dry chlorination, it has to be continuously detached from the reactor walls and remixed. In addition, the continuous taking of samples is necessary, in order to determine the degree of chlorination, so that the supply of chlorine can be interrupted at the correct time. The process is also problematical because of corrosion.

The conversion of tere- and isophthalic acid diamides to the corresponding bis-N-chloramides through chlorination in an aqueous medium of mineral acids if known from German Patent Disclosure No. 2 313 548. The application of this process known for the two above-mentioned aromatic dicarboxylic acid amides was not obvious to the extent that the expert had to conclude from the statements in Rayon plus Synthetic plus Rayon Staple, that, in the presence of excess hydrochloric acid, the aliphatic N-chloramides would again dissociate into amides and chlorine (loc. cit., page 8 at the bottom).

GENERAL DESCRIPTION OF THE INVENTION

The object of the present invention is a process for the preparation of bis-N-chloramides of saturated, aliphatic dicarboxylic acids in accordance with which dicarboxylic acid diamides of the general formula $$H_2N-CO-X-CO-NH_2$$

wherein X represents a straight-chain or branched-chain aliphatic residue with four to forty carbon atoms, are chlorinated in aqueous mineral acids at temperatures from 0° to 40° C.

Suitable starting materials include, for example, the diamides of the following dicarboxylic acids; adipic acid, pimelic acid, suberic acid, azelaic acid, sebacic acid, nonane dicarboxylic acid, decane dicarboxylic acid, and hendecane dicarboxylic acid.

Dilute aqueous hydrochloric acid (1% to 25%) and sulfuric acid (1% to 10%) are for example suitable as aqueous media of mineral acids. In the process pursuant to the invention it is possible to start out with a neutral, aqueous suspension of the amides; thereby, the hydrogen chloride formed as by-product during chlorination dissolves in the reaction mixture and conversion thus takes place in a dilute, aqueous-hydrochloric acid medium. Preferably, a start is made with a dilute, hydrochloric acid suspension of the diamide.

According to another preferred version of the process pursuant to the invention, chlorination takes place in the presence of an inorganic salt. Suitable salts are for example alkali chlorides and chlorides of the alkaline earth metals, as well as alkali sulfates and sulfates of the alkaline earth metals. Examples of suitable salts include the chlorides and sulfates of sodium, potassium, lithium, rubidium, caesium, calcium, strontium and barium. Preferably, use is made of sodium chloride and sodium sulfate. The addition of a salt results in an increase in selectivity and yield. This applies in particular to bis-amides and bis-N-chloramides with appreciable solubility, in which cases separation of the reaction product is in addition facilitated. In the case of this version of the process pursuant to the invention, one preferably starts out with a suspension of the diamide in a hydrochloric acid-saturated sodium chloride solution.

Chlorination of the diamides proceeds in an exothermic manner. The process pursuant to the invention is carried out at temperatures from 0° to 40° C. The use of higher temperatures is disadvantageous to the extent that under these conditions noticeable quantities of dicarboxylic acids are formed by means of hydrolysis. For economic reasons, chlorination is preferably carried out at 5° to 30° C., whereby it is possible to remove the reaction heat by means of cooling with water.

The process pursuant to the invention can be carried out at normal pressure, as well as under an elevated pressure. It is true that the required reaction time declines with increasing pressure, but, for economic reasons, the preferred pressure range is between about 6 and 10 kg/cm$^2$.

If, in the process pursuant to the invention, chlorination takes place in the heterogeneous phase, care must be taken that the suspension is properly mixed. Dilution of the reaction mixture should then at least be such that the latter can be stirred without difficulty, or mixed in some other way. The preferred dilution of the reaction batch amounts to about 100 to 200 grams of amide per liter of water or aqueous mineral acid.

When mentioned process conditions are maintained, chlorination is terminated after about ten minutes to 2.5 hours. The amide is practically quantitatively converted into the N,N'-dichloramide, even if there has been no solution in the interim. The products can be separated in the simplest way, e.g. through filtering or centrifuging. After washing, e.g. with cold water, and drying at e.g. 70° C. in a vacuum, one obtains them in highest purity.

The compounds obtainable pursuant to the process of the invention represent valuable intermediate products; for example, they can be used for the preparation of diurethanes, diureas, diamines and di-isocyanates.

Compared with the known process, the process pursuant to the invention is distinguished by the fact that it results in highly pure bis-N-chloramides with very high to almost quantitative yields. For example, according to the process described in Rayon plus Synthetics plus Rayon Staple, the crude yield obtained in the case of adipic acid-N-chloramide is only 61%, for suberic acid-N-chloramide it is only 62% and for sebacic acid-N-chloramide it is only 37% (loc. cit., page 50). Furthermore, the process pursuant to the invention is superior to the extent that it is simple and harmless.

DESCRIPTION OF THE PREFERRED EMBODIMENTS

The following examples illustrate the invention, but are not to be regarded as limiting:

EXAMPLE 1

75.2 g (0.33 mol) dodecane dicarboxylic acid diamide were suspended in 2.5 liters of semi-concentrated hydrochloric acid and, in the course of 2.5 hours, converted to bis-N-chloramide at 24° to 26° C. with a vigorous supply of chlorine (fine distribution through a glass fit). After separation by suction, washing until neutral with water, and drying it was possible to isolate 91.6 g (=97.8% of the theory) of the desired dodecane-1,12-bis-N-chloramide from the suspension as a white powder with a melting point of 122° to 126° C.

EXAMPLE 2

Analogous to Example 1, 73 g (0.35 mol) of sebacic acid diamide were finely suspended in 3 liters of semi-concentrated hydrochloric acid and converted in the course of 2.5 hours at 10° C. through introduction of a vigorous stream of chlorine. Direct isolation from the suspension of 82.3 g (−98% of the theory) of sebacic acid-bis-N-chloramide as a colorless powder with a melting point of 133° to 136° C. was possible.

EXAMPLE 3

56 g (0.325 mol) of suberic acid diamide were dissolved in one liter of semi-concentrated hydrochloric acid and subjected to chlorination at 5° C. in the course of 2.5 hours. On this occasion, a fine, white precipitate was formed in the course of the reaction in the initially clear solution of the diamide in hydrochloric acid. This precipitate was dried by suction, washed until neutral with very little ice water and acetone, and consisted of the desired suberic acid-bis-N-chloramide; yield: 34.2 g (43.6% of the theory).

Careful concentration of the reaction solution by means of evaporation permitted isolation of a further 61 g (46% of the theory) of bis-N-chloramide with a melting point of 149° to 152° C. (with decomposition). Total yield: 89.6% of the theory of suberic acid-bis-N-chloramide. Isolation of the originally dissolved N-chloramide was also possible by means of salting out with NaCl.

EXAMPLE 4

56 g (0.325 mol) of suberic acid diamide were suspended in one liter semi-concentrated hydrochloric acid saturated with NaCl and chlorinated in the course of 2.5 hours at 5° C. After this period, the fine, white precipitate was isolated by suction, washed until neutral with a little ice water, and dried. The product obtained in this manner was pure suberic acid-bis-N-chloramide; yield: 90.7%.

EXAMPLE 5

21.6 g adipic acid diamide (0.15 mol) were dissolved in 80 ml of semi-concentrated hydrochloric acid, whereupon chlorine was introduced at 10° C. in the course of 1 hour. A fine, white precipitate began to separate from the reaction solution after about 15 minutes. It was isolated after termination of the reaction and washed with very little ice water. After drying, there remained 6.69 g (=20.9% of the theory) of adipic acid-bis-N-chloramide. Melting point: 155° to 160° C.

Careful concentration permitted the isolation of an additional 19.5 g (=61% of the theory) of adipic acid-bis-N-chloramide from the filtrate. Total yield of adipic acid-bis-N-chloramide: 81.9% of the theory.

EXAMPLE 6

21.6 g of adipic acid diamide (0.15 mol) were dissolved in 80 ml of a 5% by weight, aqueous hydrochloric acid saturated with sodium chloride, followed by the introduction of chlorine at 10° C. in the course of 1 hour. The adipic acid-bis-N-chloramide was filtered off after termination of the reaction, washed with a little ice water, and subsequently dried. The yield amounted to 91.5% of the theory.

What is claimed is:

1. A process for the preparation of a bis-N-chloramide of a saturated aliphatic dicarboxylic acid, which comprises chlorinating a saturated aliphatic dicarboxylic acid diamide of the formula

H₂N-CO-X-CO-NH₂ wherein X is an aliphatic residue having 4 to 40 carbon atoms, with chlorine in a medium consisting essentially of an aqueous inorganic acid, at a temperature between 0° and 40° C.

2. The process of claim 1 in which X is a straight-chain aliphatic residue.

3. The process of claim 1 in which X is a branched-chain aliphatic residue.

4. The process of claim 1 in which said chlorination is carried out in the presence of an inorganic salt.

5. The process of claim 1 in which said diamide is chlorinated in the form of a dilute hydrochloric acid suspension.

6. The process of claim 1 in which said diamide is chlorinated in the form of a suspension in dilute hydrochloric acid saturated with sodium chloride.

* * * * *